(12) United States Patent
Woermann

(10) Patent No.: US 11,583,447 B2
(45) Date of Patent: Feb. 21, 2023

(54) APPARATUS FOR PROTECTING EYES FROM RADIATION

(71) Applicant: Bernd Woermann, Dresden (DE)

(72) Inventor: Bernd Woermann, Dresden (DE)

(*) Notice: Subject to any disclaimer, the term of this patent is extended or adjusted under 35 U.S.C. 154(b) by 332 days.

(21) Appl. No.: 16/465,719

(22) PCT Filed: Dec. 7, 2017

(86) PCT No.: PCT/EP2017/081858
§ 371 (c)(1),
(2) Date: May 31, 2019

(87) PCT Pub. No.: WO2018/104465
PCT Pub. Date: Jun. 14, 2018

(65) Prior Publication Data
US 2019/0290491 A1    Sep. 26, 2019

(30) Foreign Application Priority Data
Dec. 7, 2016 (DE) .......................... 102016123634.9

(51) Int. Cl.
*A61F 9/02* (2006.01)
*A61B 6/10* (2006.01)
(Continued)

(52) U.S. Cl.
CPC .............. *A61F 9/022* (2013.01); *A61B 6/107* (2013.01); *A61F 9/027* (2013.01);
(Continued)

(58) Field of Classification Search
CPC ..... A61F 9/022; A61F 9/027; G02B 27/0172; G02B 2027/0178; G02B 2027/0158;
(Continued)

(56) References Cited

U.S. PATENT DOCUMENTS 4,603,442 A * 8/1986 Barfield .................... A61F 9/02
2/446
5,619,754 A * 4/1997 Thurwanger .......... A42B 3/085
2/416
(Continued)

FOREIGN PATENT DOCUMENTS

CN    102573720 B    3/2015
EP      419854 A1    4/1991
(Continued)

OTHER PUBLICATIONS

Piehler et al. (English Translation of WO 2018028759 A1) (Year: 2016).*
(Continued)

*Primary Examiner* — Talha M Nawaz
(74) *Attorney, Agent, or Firm* — Heslin Rothenberg Farley & Mesiti, P.C.

(57) ABSTRACT

The invention relates to an apparatus for protecting eyes from radiation, in particular for protecting the lenses of the eyes of medical personnel from x-ray radiation or other ionizing radiation during medical examinations. The apparatus is easy to handle and ensures shielding of the eyes from x-ray radiation, but nonetheless offers the best working and viewing conditions for the wearer. This is achieved by a housing made of a shell-type frame, which encloses the eye area and laterally the temples of the wearer, and a support device for placement on the head and with a nose rest for positioning on the bridge of the nose. The frame includes a frontal opening, in which a shield opaque to x-ray radiation is fitted, and at least one video playback device is arranged on the rear side of the shield, facing toward the eyes, inside the frame, and being coupled to an optical recording device or a camera, which is arranged on the side of the shield that faces away from the wearer.

19 Claims, 2 Drawing Sheets

Figure 1:
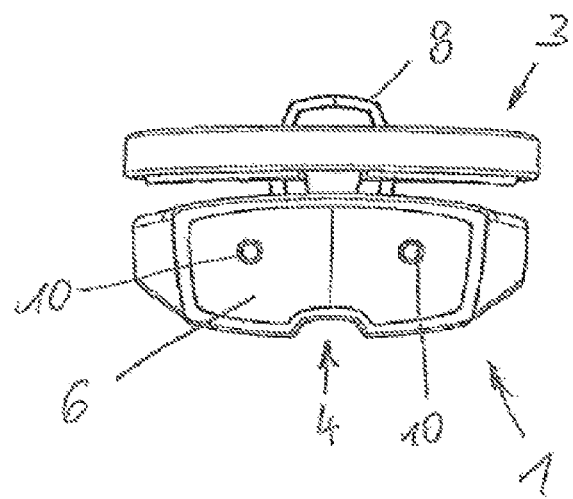

(51) Int. Cl.
*H04N 13/189* (2018.01)
*H04N 13/344* (2018.01)
*H04N 13/239* (2018.01)
*G02B 27/01* (2006.01)

(52) U.S. Cl.
CPC ....... *G02B 27/0172* (2013.01); *H04N 13/189* (2018.05); *H04N 13/239* (2018.05); *H04N 13/344* (2018.05); *G02B 2027/0134* (2013.01); *G02B 2027/0158* (2013.01); *G02B 2027/0178* (2013.01)

(58) Field of Classification Search
CPC ......... G02B 2027/0134; H04N 13/189; H04N 13/344; H04N 13/239; A61B 6/107
See application file for complete search history.

(56) References Cited

U.S. PATENT DOCUMENTS

| | | | |
|---|---|---|---|
| 8,334,899 B1* | 12/2012 | Neil | A61F 9/022 348/67 |
| 8,588,448 B1 | 11/2013 | Rickards et al. | |
| 2005/0128735 A1* | 6/2005 | Atkins | A61B 3/12 362/105 |
| 2011/0075265 A1* | 3/2011 | Alekseyev-Popov | G02B 23/125 359/630 |
| 2011/0214082 A1 | 9/2011 | Osterhout et al. | |
| 2012/0306725 A1* | 12/2012 | Hilkes | G09G 5/00 345/8 |
| 2013/0113900 A1* | 5/2013 | Ortlieb | A61C 3/00 348/51 |
| 2013/0249778 A1* | 9/2013 | Morimoto | G02B 27/0176 345/8 |
| 2014/0266986 A1* | 9/2014 | Magyari | G02B 7/04 345/8 |
| 2014/0333773 A1 | 11/2014 | Davis et al. | |
| 2015/0077712 A1* | 3/2015 | Geertsen | A61F 9/025 2/442 |
| 2015/0103334 A1* | 4/2015 | Quant | G01J 3/0221 356/51 |
| 2015/0146843 A1* | 5/2015 | Steinhauser | A61B 6/46 378/4 |
| 2015/0150725 A1* | 6/2015 | Piombini | G02B 27/0172 2/12 |
| 2016/0349539 A1* | 12/2016 | Waisman | G06F 3/04847 |
| 2017/0004895 A1* | 1/2017 | Holman | G21F 3/02 |
| 2017/0017085 A1* | 1/2017 | Araki | A61B 3/12 362/105 |
| 2018/0344266 A1* | 12/2018 | Altmann | H04N 5/44504 |

FOREIGN PATENT DOCUMENTS

| | | | | |
|---|---|---|---|---|
| EP | | 780783 A1 | 6/1997 | |
| EP | | 1488768 A1 | 12/2004 | |
| WO | WO-2017182431 A1 * | | 10/2017 | ......... G02B 27/0172 |

OTHER PUBLICATIONS

International Search Report issued in PCT/EP2017/081858 dated Jul. 6, 2018.

Prof. Dr. Reinhard Loose, "Radiation Protection, so that nothing backfires", Healthcare-in-europe.com, May 29, 2013.

* cited by examiner

APPARATUS FOR PROTECTING EYES FROM RADIATION

CROSS REFERENCE TO RELATED APPLICATIONS

This application is the National Phase filing under 35 U.S.C. § 371 of International Application No.: PCT/EP2017/081858, filed on Dec. 7, 2017, and published on Jun. 14, 2018 as WO 2018/104465 A2, which claims priority to German Application No.: 102016123634.9, filed on Dec. 7, 2016. The contents of each of the prior applications are hereby incorporated by reference herein in their entirety.

The invention relates to an apparatus for protecting eyes from radiation, in particular the lenses of the eyes of medical personnel, such as diagnosticians, from x-ray radiation or other ionizing radiation during medical examinations or treatments.

BACKGROUND ART

It has been known for some time that a high level of x-ray radiation can induce turbidity of the lens of the eye and can provoke cataracts. The ICRP (International Commission of Radiological Protection) has already proposed a reduction of the permissible radiation load from 150 mSv to 20 mSv as the maximum equivalent dose of the eye per year.

The presently used protective measures for the eyes of a diagnostician are lead glass spectacles which, if correctly applied, can offer a certain level of protection. In x-ray facilities, in particular in those having multiple x-ray radiators, however, adequate shielding is difficult to implement (source: Prof. Dr. Reinhard Loose, "Strahlenschutz, damit nicht ins Auge geht [radiation protection, so that nothing backfires]", in "healthcare-in-europe.com", 29 May 2013).

Attempts have also previously been made to precisely measure the extension of the radiation fields and achieve a reduction of the radiation load for a diagnostician by way of a corresponding position of the head and/or by way of additional shields having lead glass.

For example, laser protection spectacles are disclosed in EP 0 419 854 A1, which permit a direct view of the usage location of the laser and which are formed from a spectacles frame in the form of a shell open toward the face of the spectacles wearer, in the front face of which a protective filter is inserted for each eye. Temple plates, which tightly enclose the face of the spectacles wearer together with the spectacles frame and prevent penetration of radiation behind the spectacles frame, are located laterally on the spectacles frame. The spectacles frame can consist of a light metal, such as aluminum or a suitable plastic.

However, such laser protection spectacles may not be refitted for a use under comparatively very hard x-ray radiation, so that adequate radiation protection cannot be achieved.

A similar eye protection from UV radiation in tanning devices is disclosed in EP 1 488 768 A1, which comprises a device at least partially slightly transmissive to radiation for covering the eye or both eyes, but which comprises an opening less transmissive to radiation, which permits the radiation to pass to at least one optical element, which relays optical signals to the eye. This can also be an LCD device, or mirrors for forming micro-arrays.

In addition to protecting the user from artificial UV radiation, such a device may also be used as protection from radiation of welding devices. A sufficient protection from x-ray radiation also may not be achieved using such a device.

Finally, a virtual reality playback system having an optical location recognition device is described in EP 0 780 783 A1, which consists of a helmet having an optical location recognition system, located on the front side of the helmet, for the virtual reality playback system.

Using this playback system, it is possible for the virtual world image, which is generated in front of the eye of the observer, to move correspondingly to the movement of the head. Protecting the eyes from harmful radiation is not provided here and is also not necessary.

In summary, it can be established that no practical solutions are known from the prior art, which would permit working under x-ray radiation with complete protection of the eyes with simultaneous observation of the object subjected to the x-ray radiation by a diagnostician.

SUMMARY OF THE INVENTION

The invention begins here, in that it is the object of the invention to provide an apparatus for protecting the eyes of medical personnel from radiation during medical examinations or treatments, which is easy to handle, on the one hand, and ensures shielding of the eyes from x-ray radiation or other ionizing radiation up to 100%, on the other hand, but which nonetheless offers the best working and viewing conditions for the wearer of the apparatus, such as a diagnostician.

This is achieved with an apparatus of the type mentioned at the outset in that the housing consists of a shell-type frame enclosing the eye area and laterally the temples of the wearer, the shell-type frame is provided, on the one hand, with a support device for placement on the head and, on the other hand, with a nose rest for positioning and/or fixing on the bridge of the nose of the wearer, the shell-type frame is provided with a frontal opening extending over its entire width, in which an opaque shield made of a material opaque to x-ray radiation or ionizing radiation is fitted, which reduces the radiation dose penetrating the shield to values close to zero, and at least one device for stereoscopic playback of items of video information is arranged on the rear side of the shield, facing toward the eyes, which device is coupled to an optical recording device or a camera, which is arranged on the side of the shield facing away from the eyes of the wearer.

Using this apparatus, a dynamic delay-free image can be generated in front of the eyes of the wearer, which (at least substantially) corresponds to the real image of a scene in front of the eye, wherein three-dimensional vision is possible without problems.

The shield preferably consists of lead, such as a lead plate, but can also consist of another suitable material, if the desired shielding is ensured.

In a refinement of the invention, the shield comprises the lateral temple region, so that even better radiation protection is achieved for the eyes, in particular if the wearer of the apparatus has turned his head to the side.

In a refinement of the invention, the device for stereoscopic playback of items of video information consists of display screens arranged in front of each eye inside the housing.

The device for stereoscopic playback of items of video information can also consist of a single and possibly round display screen located in front of both eyes of the wearer, or the display screen is a split-screen display screen, which generates a separate image for each eye for a stereo impression.

Alternatively, the display screen can be coupled to a shutter, which generates the images for both eyes in succession, so that a stereo impression results for the wearer of the apparatus.

In any case, a realistic stereoscopic image of the procedures in front of the apparatus is given to the wearer, which enables safe working which is harmless to the eyes for the medical personnel.

To compensate for the relatively small distance between display screen and eye, an optical unit for focusing the displayed image onto the eyes is arranged in each case between the eyes of the wearer and the display screen or the display screens. A fatigue-free observation of the display screen is thus enabled.

In a further design of the invention, the optical recording device and/or the camera is a stereoscopic camera, which is positioned directly in front of the shield.

Alternatively, two individual cameras arranged at a distance from one another and adjacent to one another can be provided in front of the shield, the distance of which to one another is settable to the eye distance. The stereoscopic impression in the wearer of the apparatus can thus be adapted to the individual conditions, and/or optimized.

Furthermore, the optical axes of the individual display screens are settable mechanically by displacement, or electronically by displacement of the images on the individual display screens, to the respective eye distance of the wearer, so that both individual images can be fused by the brain to form a single image.

To ensure a high-contrast observation of the display screen or the display screens which is free of interfering light, the shell-type frame abuts the head substantially light-tight, enclosing the eyes of the wearer.

For protection from damage and soiling, a transparent protective pane, which terminates the frame and is as clear as glass, and which is detachably connected to the shell-type frame, is arranged in front of the stereoscopic camera or the individual cameras.

In a further design of the invention, the support device for the housing is a ring which is adapted or adapts itself to the shape of the head, on which the housing having the frame is fastened in a suspended manner, wherein a headrest is arranged diametrically opposite on the ring.

To enable an individual adaptation to the head of the wearer, the ring is settable in the circumference via a catch mechanism (not shown) and the headrest is pivotably mounted on the ring.

Finally, the nose rest and the ring are provided with a cushion, at least in the contact region with the head.

In the interest of an apparatus which is as light as possible and is thus to be worn without fatigue, all components of the housing, such as the frame, the optical unit, and the protective pane, except for the shield and the video recording and playback devices with associated electronics, consist of the lightest possible plastic. The weight of the apparatus is then primarily determined by the weight of the shield.

In one particular design of the invention, the headrest is at least partially used for weight compensation for the housing connected to the ring, so that a substantially uniform pressure load of the head by the ring is achieved. To achieve this, the headrest could also be designed as a battery compartment, so that any cable connection between the apparatus and external devices can be omitted.

The particular advantage of the apparatus according to the invention can be seen in that the eye area is completely shielded in the direction of the source of the x-ray radiation by an opaque, radiation-opaque material, wherein the scene in front of the apparatus is played back in real time by the device for stereoscopic playback of items of video information on the rear side of the shield.

Additional items of information, such as blood pressure or other values, and also items of image information from other examinations or comparison values or images, etc., can also be overlaid via the display screen or the display screens.

A lead plate which completely covers the eye area, having the lowest possible weight, or another shielding material for x-ray radiation comes into consideration as the material opaque to x-ray radiation, wherein it is essential for the selection of the radiation-opaque material that the radiation dose penetrating the shield is reduced to values close to zero.

Furthermore, the side areas can also be incorporated into the radiation protection with a radiation-opaque material.

Finally, it is advantageous in the interest of fatigue-free work if the housing, or at least the shell-type frame, has an anti-reflective or matte surface on the inner side.

BRIEF DESCRIPTION OF THE DRAWING FIGURES

Figure 2:
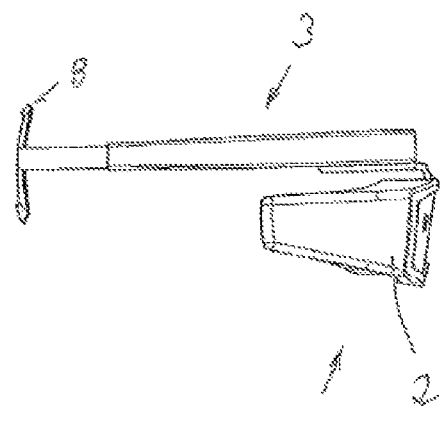
Figure 3:
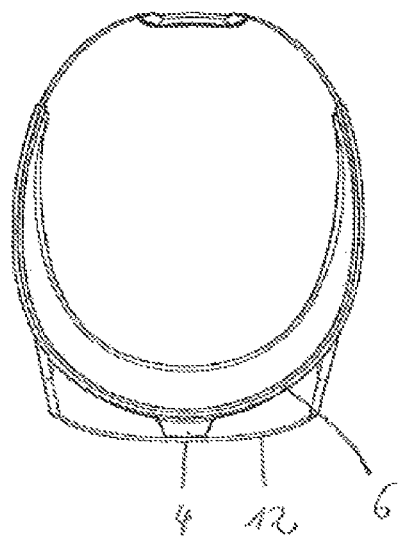
Figure 4:
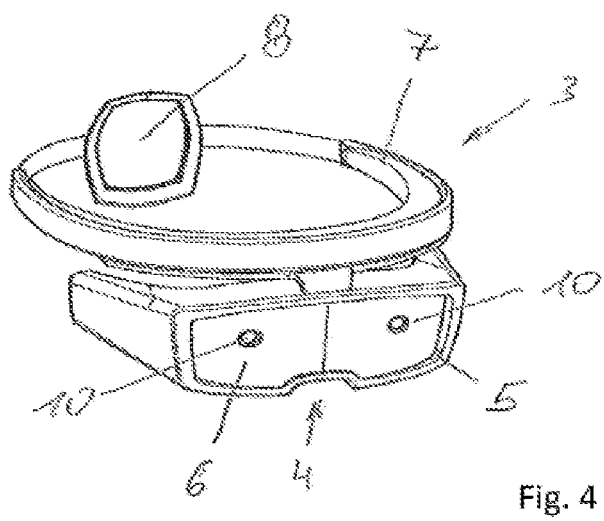
Figure 5:
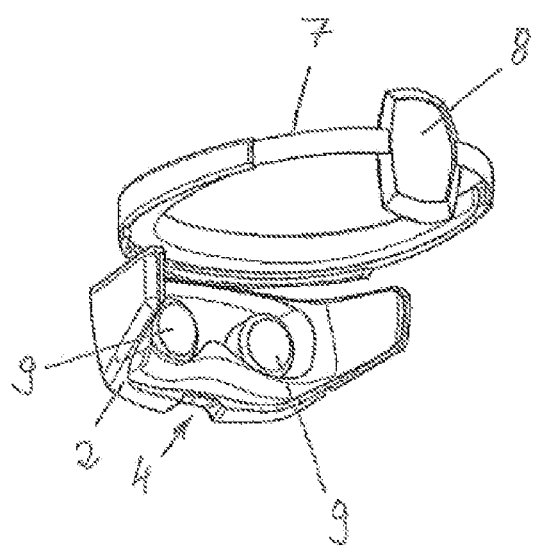

The invention will be explained in greater detail hereafter on the basis of an exemplary embodiment. In the associated figures of the drawing:

FIG. 1: shows a front view of the apparatus according to the invention for protecting eyes from radiation;

FIG. 2: shows a side view of the apparatus according to FIG. 1;

FIG. 3: shows a top view of the apparatus according to FIG. 1;

FIG. 4: shows a perspective illustration of the apparatus according to FIG. 1;

FIG. 5: shows a perspective rear view of the apparatus according to FIG. 1; and

Figure 6:
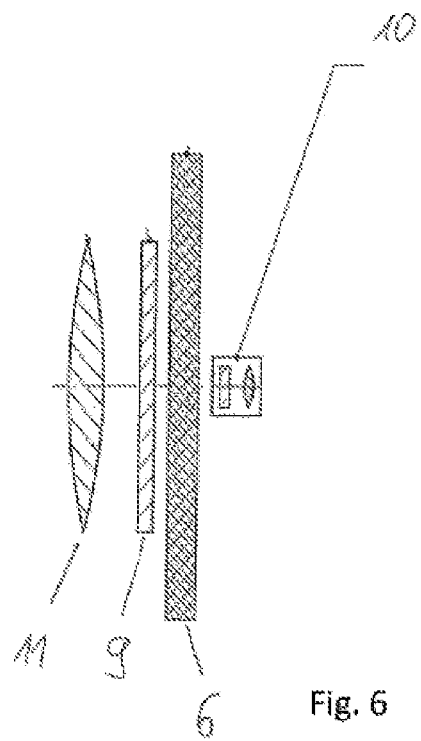

FIG. 6: shows a schematic illustration of the device for stereoscopic playback of items of video information, and an optical recording device or a camera in front of a shield.

DETAILED DESCRIPTION

The apparatus for protecting eyes from radiation comprises a housing 1, which consists of a shell-type frame 2, having an open rear side, which encloses the head including the eye area and laterally the temples of the wearer in a light-tight manner. Furthermore, the shell-type frame 2 is fastened on a support device 3 to be placed on the head and is provided with a nose rest 4 for positioning and supporting the shell-type frame 3 on the bridge of the nose of the wearer.

A frontal opening 5 extending essentially over the entire width thereof for accommodating a shield 6 made of a material opaque to x-ray radiation or ionizing radiation is located in the front region of the shell-type frame 2, i.e., on the side facing away from the head. This shield 5, which extends slightly curved, reduces the radiation dose reaching the eyes from a source for x-ray radiation to values close to zero, in particular if the shield 6 consists of a lead plate.

The shield 6 can also be manufactured from another suitable material in place of lead, if the desired shielding is ensured. A weight reduction can thus be achieved in this way.

In particular a lead plate completely covering at least the eye area having the lowest possible weight, or another shielding material for x-ray radiation comes into consideration as the shield 6, wherein it is essential for the selection of the radiation-opaque material that the radiation dose reaching the eye is reduced to values close to zero.

The shield 5 can also enclose the lateral temple region, so that even better radiation protection is achieved for the eyes, which is advantageous in particular if the wearer of the apparatus has his head turned to the side, so that the frontal shield 5 no longer faces in the direction of the source for the x-ray radiation. The x-ray radiation also cannot inadvertently radiate from the side into the eyes due to the additional lateral shielding.

Alternatively, the shell-type frame 2 can also be manufactured as a whole from a material which is opaque or hardly transmissive to x-ray radiation.

The support device 3 for the housing 1 is a ring 7, which is adapted or adapts itself to the head shape of the wearer, and on which the housing 1 having the shell-type frame 2 is fastened in a suspended manner. To enable an individual adaptation of the ring 7 to the head of the wearer, it is settable in the circumference via a catch mechanism (not shown) or the like.

Furthermore, a preferably pivotably mounted headrest 8, which is supported on the back of the head and enables secure wearing of the apparatus, is located on the ring 7, diametrically opposite to the housing 1.

The headrest 8 can also be at least partially used as a counterweight for the housing 1 connected to the ring 7. For example, a battery compartment could be housed for this purpose in the headrest 8, so that a more uniform pressure load of the head by the ring 7 is achieved.

For better load distribution, one or more support belts fastened on the ring 7 can also be provided, which press against the head of the wearer from above when the apparatus is put on.

In addition, the nose rest 4 and the ring 7 can be provided with cushioning at least in the contact region with the head, i.e., the support points.

At least one playback device 9 for the stereoscopic playback of items of video information, which is coupled to an optical recording device 10 or a camera arranged on the side of the shield 6 facing away from the eyes of the wearer, is located on the rear side of the shield 6 facing towards the eyes of the wearer, wherein the images and image sequences recorded by the recording device 10 are transmitted directly and without delay to the playback device 9.

This arrangement enables a dynamic image to be generated in front of the eyes of the wearer of the apparatus, which (at least substantially) corresponds to the real image of a scene in front of the eye, wherein three-dimensional vision is possible without problems, wherein the x-ray radiation reaching the apparatus cannot reach the eyes of the wearer, so that nonhazardous working is possible.

The playback device 9 can consist of a display screen positioned in each case in front of each eye inside the shell-type frame 2, which can optionally also have a round outline.

Alternatively, the playback device 9 can also consist of a single display screen located in front of both eyes of the wearer, which is coupled to a shutter, which generates the images for both eyes in succession, so that a stereo impression results for the wearer of the apparatus.

The playback device 9 can also be a split-screen display screen, which generates a separate image for each eye for a stereo impression.

In any case, a realistic stereoscopic image of the procedures in front of the apparatus is given to the wearer, which enables safe work which is nonhazardous to the eyes for the medical personnel.

To compensate for the relatively small distance between display screen and eye, or to compensate for defective vision, an optical unit 11 for focusing the displayed image onto the eyes is arranged in each case between the eyes of the wearer and the display screen or the display screens, whereby fatigue-free observation of the display screen is enabled.

Furthermore, it is expedient in the interest of good stereoscopic playback to set the optical axes of the individual display screens mechanically by displacement, or electronically by displacement of the images on the individual display screens, to the respective eye distance of the wearer.

The optical recording device 10 or the camera can be a stereoscopic camera, which is positioned directly in front of the shield 6.

Alternatively, two individual cameras arranged at a distance in relation to one another and adjacent to one another can also be provided in front of the shield 6, the distance of which in relation to one another can be settable to the eye distance. The stereoscopic impression in the wearer of the apparatus can thus be adapted to the individual conditions.

The electrical connection between the playback device 9 and the recording device 9 for power supply and information transmission takes place by means of suitable rewiring, which is laid around the shield 6.

To ensure observation of the display screen or the display screens free of interfering light, the shell-type frame 2 abuts the head in an essentially light-tight manner, enclosing the eyes of the wearer.

Since reflections or light reflections, caused by the playback device 10, are also to be avoided, the housing 1 or at least the shell-type frame is to have an anti-reflective or matte surface on the inner side, which can also be achieved, for example, by a matte or matte-black coating. A substantially fatigue-free use of the apparatus according to the invention by a diagnostician is thus ensured. For protection from damage and soiling, and also for design reasons, a transparent protective pane 12, which is as clear as glass and terminates the shell-type frame 2 to the front, and which can be detachably connected to the shell-type frame 2, is arranged in front of the stereoscopic camera or the individual cameras.

The particular advantage of the apparatus according to the invention can be seen in that the eye area is completely shielded at least in the direction of the source of the x-ray radiation using an opaque, radiation-opaque material, wherein the scene in front of the apparatus is played back in real time by the playback device 10 for stereoscopic playback of items of information on the rear side of the shield 6.

In the interest of the lightest possible apparatus, which is thus to be worn without fatigue, all components of the housing 1, such as the shell-type frame 2, the optical unit 11, and the protective pane 12, with the exception of the shield and the video recording and playback devices with associated electronics, consist of the lightest possible plastic material.

Items of additional information such as blood pressure or other values, and also items of image information from other examinations, etc., can also be overlaid via the playback device 10.

LIST OF REFERENCE NUMERALS 1 housing
2 shell-type frame 3 support device
4 nose rest
5 opening
6 shield
7 ring
8 headrest
9 playback device
10 recording device
11 optical unit
12 protective pane

The invention claimed is:

1. An apparatus for protecting a wearer from x-ray radiation, in particular the lenses of the eyes of medical personnel during medical examinations, comprising:
 a housing positionable in front of the eye area on a head of the wearer having an open rear side and a front side that encloses the eye area and the temples of the wearer in a light tight manner,
 wherein the housing is provided with a support device for supporting the weight of the apparatus via the wearer's head, and with a nose rest for positioning and/or fixing on the bridge of the nose of the wearer, and is void of earpieces that rest on the wearer's ears,
 wherein the support device is a ring adapted or itself adaptable to the head shape, on which the housing having the housing is fastened in a suspended manner beneath the ring, and comprising a headrest at a back side of the head at a back end portion of the ring being configured to engage portions of the back side of the head that are higher and lower than side portions of the ring that extend to the headrest, the headrest being configured as a counterweight to the housing on an opposing side of the ring as the housing,
 wherein the nose rest and the ring comprise cushioning arranged to contact the wearer when the apparatus is worn by the wearer,
 wherein the housing is provided with a frontal opening extending over its entire width, in which a shield having shielding material that is opaque to x-ray radiation is fitted, wherein the shielding material reduces the x-ray radiation dose penetrating the shield to values close to zero,
 wherein at least one playback device for the stereoscopic playback of items of video information is arranged on the rear side of the shield, facing toward the eyes, inside the housing, which playback device is coupled to at least one optical recording device or camera, which is arranged on the side of the shield that faces away from the eyes of the wearer and between bottom and top edges of the shield to record a scene in front of the wearer,
 wherein the at least one optical recording device or camera comprises two individual cameras arranged at a distance to one another and adjacent to one another, and positioned directly in front of the shield, the distance of said cameras in relation to one another being settable by the wearer to a respective eye distance of the wearer,
 wherein the at least one playback device for the stereoscopic playback of items of video information comprises a display screen arranged in front of each eye of the wearer, the optical axes of the individual display screens being settable mechanically by displacing the display screens, or electronically by displacing the images, to a respective eye distance of the wearer, and
 wherein the at least one optical recording device or camera and the at least one playback device for the stereoscopic playback of items of video information are configured to generate a dynamic image on the display screens that corresponds to the real image of the scene according to the eyes of the wearer during x-ray radiation.

2. The apparatus as claimed in claim 1, wherein the shield material comprises a lead plate or another suitable material.

3. The apparatus as claimed in claim 1, wherein the shield encloses the lateral temple region of the head.

4. The apparatus as claimed in claim 1, wherein the playback device for the stereoscopic playback of items of video information comprises a single display screen positioned in front of both eyes of the wearer.

5. The apparatus as claimed in claim 4, wherein the display screen is a split-screen display screen, which generates a separate image for each eye for a stereo impression.

6. The apparatus as claimed in claim 4, wherein the display screen is coupled to a shutter, which generates the images for both eyes in succession, so that a stereo impression results.

7. The apparatus of claim 1, wherein an optical unit for focusing the displayed images is arranged between the eyes of the wearer and the display screens.

8. The apparatus of claim 1, wherein the optical recording device or the camera is a stereoscopic camera, which is arranged directly in front of the shield.

9. The apparatus of claim 1, wherein the housing is configured to press against the head in an essentially light-tight manner, enclosing the eyes of the wearer.

10. The apparatus of claim 1, wherein a transparent protective pane, which is as clear as glass and terminates the housing, is arranged in front of the stereoscopic camera or the individual cameras.

11. The apparatus of claim 1, wherein the ring is settable in the circumference via a catch mechanism.

12. The apparatus of claim 1, wherein the headrest is pivotably mounted on the ring.

13. The apparatus of claim 1, wherein all components, such as the housing, the housing, the optical unit, and the protective pane, except for the shield and the video recording and playback devices with associated electronics, consist of plastic.

14. The apparatus of claim 1, wherein the housing, or at least the housing, has an anti-reflective or matte surface on the inner side.

15. The apparatus of claim 1, wherein the headrest is at least partially designed as a weight compensation for the housing connected to the ring.

16. The apparatus of claim 1, wherein the headrest is configured as a counterweight such that the ring applies a substantially uniform load to the wearer about the head of the wearer.

17. The apparatus of claim 16, wherein the headrest further comprises a battery compartment configured to engage with one or more battery and provide power for the apparatus.

18. The apparatus of claim 1, wherein the headrest further comprises a battery compartment configured to engage with one or more battery and provide power for the apparatus.

19. The apparatus of claim 1, wherein the housing is configured such that it does not extend over and engage a top portion of the head of the wearer.

* * * * *